US007501073B2

(12) United States Patent
Wen et al.

(10) Patent No.: US 7,501,073 B2
(45) Date of Patent: Mar. 10, 2009

(54) METHODS FOR PRODUCING METALLIC IMPLANTS HAVING ROUGHENED SURFACES

(75) Inventors: Hai Bo Wen, Warsaw, IN (US); Panjian Li, Fort Wayne, IN (US); Todd Smith, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 383 days.

(21) Appl. No.: 10/770,157

(22) Filed: Feb. 2, 2004

(65) Prior Publication Data

US 2004/0167633 A1    Aug. 26, 2004

Related U.S. Application Data

(63) Continuation-in-part of application No. 10/373,390, filed on Feb. 24, 2003, now abandoned.

(51) Int. Cl.
*B44C 1/22* (2006.01)
*C03C 15/00* (2006.01)
*C03C 25/68* (2006.01)
*C23F 1/00* (2006.01)
*C25F 3/00* (2006.01)

(52) U.S. Cl. .................................. 216/109; 623/23.55
(58) Field of Classification Search ................. 216/109; 623/11.11, 23.29, 23.5, 23.55, 23.57, 23.6, 623/23.53
See application file for complete search history.

(56) References Cited

U.S. PATENT DOCUMENTS

| 2,711,364 | A |   6/1955 | Beach |
|---|---|---|---|
| 2,981,610 | A |   4/1961 | Snyder et al. |
| 3,106,499 | A | 10/1963 | Kendall |
| 3,844,859 | A | 10/1974 | Roni |
| 3,855,638 | A | 12/1974 | Pilliar |
| 3,960,741 | A |   6/1976 | Gabrail |
| 4,314,876 | A |   2/1982 | Kremer et al. |
| 4,550,448 | A * | 11/1985 | Kenna ....................... 623/23.6 |
| 4,554,050 | A | 11/1985 | Minford et al. |
| 5,209,829 | A |   5/1993 | Gondel et al. |
| 5,236,459 | A |   8/1993 | Koch et al. |

(Continued)

FOREIGN PATENT DOCUMENTS

WO    WO 01/66479 A1    9/2001

(Continued)

OTHER PUBLICATIONS

Brady et al. "Chemistry: the study of Matter and its Changes" pp. 706-707, John Wiley and Sons Inc. 1993.*

*Primary Examiner*—Roberts Culbert
(74) *Attorney, Agent, or Firm*—Leydig, Voit & Mayer, Ltd.

(57) ABSTRACT

The invention provides a method of providing a metallic orthopaedic implant with a micron or nanometer-scale surface roughness to facilitate acceptance of tissue and bone growth or apposition after implantation while maintaining the structural integrity of the orthopaedic implant. The invention also provides a metallic orthopaedic implant comprising a metallic body and metallic elements adhered to a portion of the surface of the metallic body to define a three-dimensional porous surface geometry, wherein at least some of the metallic elements have a micron or nanometer-scale surface roughness.

30 Claims, 8 Drawing Sheets

U.S. PATENT DOCUMENTS

| | | | |
|---|---|---|---|
| 5,258,098 A | 11/1993 | Wagner et al. | |
| 5,307,594 A | 5/1994 | Panchison | |
| 5,376,236 A | 12/1994 | Hanson et al. | |
| 5,439,569 A | 8/1995 | Carpio | |
| 5,456,723 A | 10/1995 | Steinemann et al. | |
| 5,545,262 A | 8/1996 | Hardee et al. | |
| 5,571,188 A * | 11/1996 | Ellingsen et al. | 427/2.26 |
| 5,607,480 A | 3/1997 | Beaty | |
| 5,826,586 A | 10/1998 | Mishra et al. | |
| 5,843,289 A | 12/1998 | Lee et al. | |
| 5,846,374 A * | 12/1998 | Parab et al. | 156/345.11 |
| 5,855,612 A | 1/1999 | Ohthuki et al. | |
| 5,876,453 A | 3/1999 | Beaty | |
| 6,136,369 A | 10/2000 | Leitao et al. | |
| 6,143,948 A | 11/2000 | Leitao et al. | |
| 6,146,686 A | 11/2000 | Leitao | |
| 6,183,255 B1 | 2/2001 | Oshida | |
| 6,207,218 B1 | 3/2001 | Layrolle et al. | |
| 6,261,322 B1 | 7/2001 | Despres, III et al. | |
| 6,319,286 B1 | 11/2001 | Fernandez et al. | |
| 6,582,470 B1 | 6/2003 | Lee et al. | |
| 7,048,870 B1 * | 5/2006 | Ellingsen et al. | 216/109 |

FOREIGN PATENT DOCUMENTS

WO  WO 03/008657 A1  1/2003

* cited by examiner

METHODS FOR PRODUCING METALLIC IMPLANTS HAVING ROUGHENED SURFACES

CROSS-REFERENCE TO RELATED PATENT APPLICATIONS

This patent application is a continuation-in-part of copending U.S. patent application Ser. No. 10/373,390, filed Feb. 24, 2003.

FIELD OF THE INVENTION

This invention pertains to metallic orthopaedic implants and methods for producing the same.

BACKGROUND OF THE INVENTION

The success of orthopaedic implants surgically implanted in living bone substantially depends on achieving and maintaining an enduring bond between the confronting surfaces of the implant and the host bone. Surgical procedures for preparing living bone to receive a surgically implanted orthopaedic device have been known for twenty years or more, but the ideal properties of the surface of the orthopaedic implant which confronts the host bone and processes of preparing the implant surface are the subjects of considerable disagreement.

It is generally known that the osseointegration of metallic orthopaedic implants is dependent, in part, on the attachment and spreading of osteoblast-like cells on the surface of the orthopaedic implant. Furthermore, studies suggest that such cells will more readily attach to rough or porous surfaces, as compared to smooth surfaces. To that end, several attempts have been made to provide metallic orthopaedic implants having roughened and/or porous surfaces to aid in the osseointegration of the implants.

For example, U.S. Pat. No. 5,236,459 describes a process for forming an implant surface having "anchoring areas" in which a high-pressure liquid jet is used to remove a portion of the metal from the implant surface. The diameter of the "anchoring areas" can be varied from 0.5 to 1.5 mm.

U.S. Pat. No. 5,307,594 describes another method for forming a textured surface on an orthopaedic implant. This method entails the application of a resilient mask, which contains several openings, to the surface of the implant and then subjecting the implant to high pressure blasting using an erosive blasting media, such as metal oxides particles. While this process can be used to produce implant surfaces having roughened surfaces, particles of the blasting media can become imbedded in the surface of the implant. Furthermore, it is believed that these particles can adversely affect the osseointegration of the orthopaedic implant following implantation.

Each of the above-described methods provides a metallic implant having a roughened surface consisting of surface features that are generally greater than 20 µm in size. While an orthopaedic implant having such surface features may exhibit improved osseointegration as compared to a smooth metallic implant, it is believed that osseointegration will be greatly improved if the implant surface includes smaller surface features (i.e., less than 20 µm in size).

In addition to the mechanical methods of providing a roughened surface described above, various chemical etching methods have been used to texture the surface of orthopaedic implants. For instance, U.S. Pat. No. 5,876,453 describes a two-step process in which a hydrofluoric acid solution (10-50% HF) is used to remove the native oxide surface layer formed on the metallic implant, and a second acid treatment is used to further etch the metal to provide a roughened surface. The second acid treatment utilizes a mixture of two parts sulfuric acid (96% by weight $H_2SO_4$) and one part hydrochloric acid (37% by weight HCl). While this process and similar chemical etching processes are capable of producing roughened metallic implants having surface features less than 1 µm in size, such aggressive acid solutions often remove a relatively large amount (several hundred microns) of the metal from the surface of the implant. It accordingly becomes difficult to use such aggressive solutions without undermining the structural integrity of orthopaedic implants of smaller size.

Another method to enhance achieving and maintaining the desired bond between an implant and the host bone has been to apply metallic beads to the surface of the implant. Then, the beads are sintered to bond the beads together and to the surface of the implant. This method, described in U.S. Pat. No. 3,855,638, produces a porous surface on the metallic implant which consists of interstitial pores having an average size of approximately 20 to 200 µm uniformly distributed throughout the surface of the implant.

Implants with such a porous surface represent a widely used and effective approach. However, using mechanical methods to further roughen the porous surface of such implants is particularly problematic, as the porous surface is difficult to clean so as to satisfactorily remove particles used in the grit blasting process. Such particles can tend to collect in the interstices between adjoining beads where removal can become exceedingly difficult.

Even further, the use of previously known chemical etching methods would seriously undermine the structural integrity of orthopaedic implants of this type. Such loss in integrity can occur due to impairing and/or destroying the bonds between adjacent beads, and even dissolution and destruction of individual beads, as well as the diminishing of the bond between an individual bead and the surface of the metallic implant substrate or body.

In many applications, it is desired to provide the implant with a bioactive coating comprising, as one example, calcium phosphate materials, so as to further promote and enhance the growth of bone and/or apposition of bone at the surface of the implant after implantation. It is thus important that any surface roughening process be compatible with any desired bioactive coating and to provide adequate adherence between the bioactive coating and the metallic implant.

A need therefore exists for a method of producing a roughened surface so as to enhance osseointegration, on implants having a complex surface geometry. A need also exists for a method of producing a roughened having metallic beads without significantly and adversely affecting the structural integrity of such implants. Furthermore, a need exists for a method of producing a suitably roughened surface on a wide range of implants which can be affectively and reliably carried out and for such a method that is fully compatible with the formation of bioactive coatings.

The invention provides such a metallic orthopaedic implant and a process for producing the same. These and other advantages of the invention, as well as additional inventive features, will be apparent from the description of the invention provided herein.

BRIEF SUMMARY OF THE INVENTION

The invention provides a method of providing a metallic orthopaedic implant with a micron or nanometer-scale surface roughness to facilitate acceptance of tissue and bone growth after implantation while maintaining the structural integrity of the orthopaedic implant, which method comprises the steps of (a) providing a metallic orthopaedic implant comprising a metallic body having a surface and metallic elements adhered to a portion of the surface of the metallic body to define a three-dimensional porous surface geometry, (b) exposing at least a portion of the surface and metallic elements to an etching solution comprising (i) at least one fluoride salt, (ii) at least one acid, and (iii) water for a time and under conditions sufficient to provide the implant with micron or nanometer-scale surface roughness, while maintaining structural integrity of the orthopaedic implant, (c) cleaning at least the portion of the surface and metallic elements exposed to the etching solution, and (d) drying the metallic orthopaedic implant.

The invention further provides a metallic orthopaedic implant comprising (i) a metallic body having a surface and (ii) metallic elements adhered to a portion of the surface of the metallic body to define a three-dimensional porous surface geometry, wherein at least some of the metallic elements are interconnected to provide pores of 10 μm or more diameter between adjacent metallic elements, and wherein at least some of the metallic elements have a micron or nanometer-scale surface-etched roughness.

The invention also provides a method of providing a metallic orthopaedic implant having its native oxide surface layer with a micron or nanometer-scale surface roughness to facilitate acceptance of tissue and bone growth after implantation while maintaining the structural integrity of the orthopaedic implant, which method comprises the steps of (a) providing a metallic implant having its native oxide surface layer at least a portion thereof to be altered to provide a micron or nanometer-scale surface roughness, (b) exposing the portion of the surface layer to an etching solution comprising (i) at least one fluoride salt, (ii) at least one acid, and (iii) water for a time and under conditions sufficient to provide the implant with the micron or nanometer-scale surface roughness, while maintaining structural integrity of the orthopaedic implant, (c) cleaning at least the exposed surface, and (d) drying the metallic orthopaedic implant.

DETAILED DESCRIPTION OF THE INVENTION

Figure 1A:
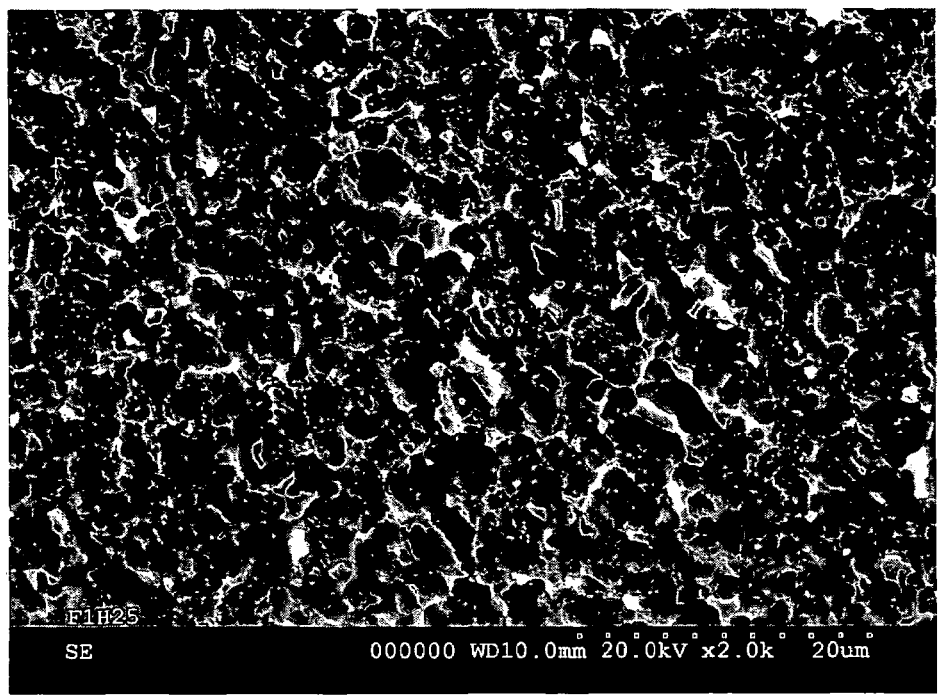
FIG. 1A is a Scanning Electron Microscopy (SEM) micrograph (2,000 times magnification) of the surface of a polished Ti6A14V coupon which has been chemically etched using the method of the invention.
Figure 1B:
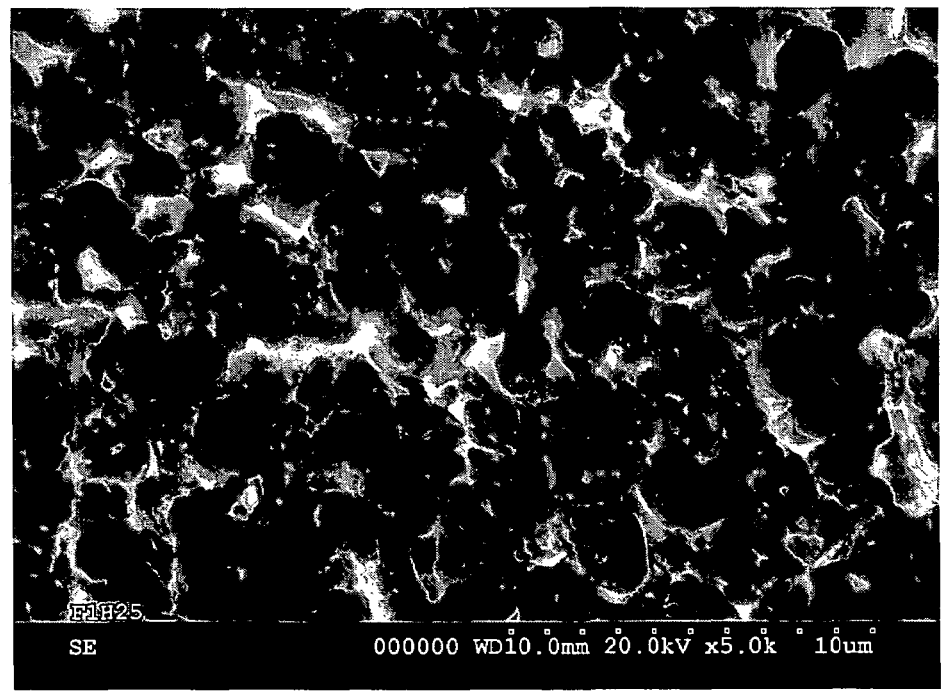
FIG. 1B is an SEM micrograph (5,000 times magnification) of the surface of the coupon shown in FIG. 1A.

The invention provides a method of providing a metallic orthopaedic implant with a micron or nanometer-scale surface roughness to facilitate acceptance of tissue and bone growth after implantation while maintaining the structural integrity of the orthopaedic implant. The method comprises the steps of (a) providing a metallic orthopaedic implant comprising a metallic body having a surface and metallic elements adhered to a portion of the surface of the metallic body to define a three-dimensional porous surface geometry, (b) exposing at least a portion of the surface and metallic elements to an etching solution comprising (i) at least one fluoride salt, (ii) at least one acid, and (iii) water for a time and under conditions sufficient to provide the implant with an altered surface having micron or nanometer-scale surface roughness without structural impairment of the orthopaedic implant, (c) cleaning at least the altered surface, and (d) drying the thus etched metallic orthopaedic implant.

As utilized herein, the term "micron or nanometer-scale surface roughness" is used to denote a surface roughness value ($R_a$) of about 10 μm or less. The term "micron-scale surface roughness" especially is used to denote a surface roughness value ($R_a$) of between about 100 nm and about 10 μm. The term "nanometer-scale surface roughness" is used to denote a surface roughness value ($R_a$) of about 100 nm or less. According to American Society of Mechanical Engineers (ASME) standard B46.1-1995, the surface roughness ($R_a$) is a measure of the average deviation of the roughness profile from the mean line. The surface roughness ($R_a$) can be measured using any of the techniques set forth in ASME standard B46.1-1995 and is considered to be within the ranges set forth herein when so determined by any of the techniques.

The metallic orthopaedic implants suitable for use in the invention are not particularly limited. Generally, the metallic orthopaedic implants comprise a metallic body having a surface and a plurality of metallic elements adhered to a portion of the surface of the metallic body. The metallic elements form a three-dimensional porous surface geometry on the surface of the metallic orthopaedic implant, and at least a portion of the metallic elements are interconnected to form pores between adjacent metallic elements (i.e., interstitial pores). These pores can range in size from about 10 μm to about 200 μm and, in some cases, up to 750 μm. The methods used to produce the metallic orthopaedic implants suitable for use in the invention are not particularly limited. One suitable method is described in U.S. Pat. No. 3,855,638. In this method, a plurality of metallic elements are coated onto the surface of the metallic implant, and then the implant is sintered to fuse the metallic elements to the body of the implant and to each other. Typically, this method yields a metallic implant having interstitial pore sizes of greater than 20 μm.

The metallic body of the implant can comprise any metal that is suitable for implantation into the human body, i.e., any biocompatible metal. Suitable metals include, but are not limited to, titanium, tantalum, and stainless steel. Preferably, the metallic body comprises a metal selected from the group consisting of titanium, titanium alloys, tantalum, tantalum alloys, stainless steel, and cobalt-chromium alloys (e.g., cobalt-chromium-molybdenum alloy). Typically, the metallic elements adhered to the surface of the metallic body of the implant comprise titanium. However, the metallic elements can be made from any biocompatible metal including, but not limited to, one or metals selected from the group consisting of titanium, titanium alloys, tantalum, tantalum alloys, stainless steel, and cobalt-chromium alloys (e.g., cobalt-chromium-molybdenum alloy).

The metallic elements adhered to the surface of the metallic body of the implant can be provided in any suitable form. Generally, the metallic elements comprise metallic particles, metallic fibers, metallic wires, or combinations thereof. The metallic elements can also be arranged in a predetermined pattern. For instance, a plurality of metallic fibers or wires can be arranged to form a mesh, which can be adhered to the surface of the implant's metallic body. In a preferred embodiment, the metallic elements comprise metallic particles. More preferably, the metallic particles comprise metallic beads. These metallic particles or metallic beads can be any suitable size. Typically, the size of the metallic particles or metallic beads is from about 40 μm to several millimeters.

The etching solution used in the inventive method comprises at least one fluoride salt, at least one acid, and water. In a preferred embodiment, the etching solution further comprises at least one chemically inert, water-soluble salt. The fluoride salts, acids, and chemically inert, water soluble salts suitable for use in the invention are not particularly limited. However, the fluoride salt and chemically inert, water-soluble salt should be soluble in an acidic, aqueous environment.

In a preferred embodiment, the fluoride salt is selected from the group consisting of ammonium fluoride, copper fluoride (cupric fluoride), potassium fluoride, sodium fluoride, zinc fluoride, and mixtures thereof. The fluoride salt can be present in the etching solution in any suitable concentration. Typically, the concentration of the fluoride salt is about 0.01 wt. % or more, preferably about 0.05 wt. % or more, and more preferably about 0.1 wt. % or more (e.g., about 0.5 wt. % or more). Furthermore, the concentration of the fluoride salt can be as high as the solubility limit of the fluoride salt in the etching solution, but typically is about 10 wt. % or less, preferably about 3 wt. % or less, more preferably about 2 wt. % or less, and most preferably about 1.5 wt. % or less.

Acids suitable for use in the invention include organic acids and mineral acids. Preferably, the acid is selected from the group consisting of hydrochloric acid, nitric acid, sulfuric acid, acetic acid, lactic acid, perchloric acid, oxalic acid, tartaric acid, phosphoric acid, and mixtures thereof. The acid can be present in the etching solution in any suitable concentration. Those of ordinary skill in the art will readily appreciate that the suitable concentration of acid in the etching solution can depend, at least in part, on the particular acid being used. For example, the range of suitable concentrations for hydrochloric acid in the etching solution could be different from the range of suitable concentrations for sulfuric acid. Typically, the acid concentration is about 0.001 N or more, preferably about 0.01 N or more, and more preferably about 0.1 N or more. Furthermore, the concentration of the acid is typically about 10 N or less, more preferably about 5 N or less, and most preferably about 4 N or less (e.g., about 2 N or less, or about 1 N or less).

The etching solution used in the inventive method can comprise any suitable chemically inert, water-soluble salt. As utilized herein, the term "chemically inert" refers to a salt that does not chemically react to an appreciable extent with the other components present in the etching solution. Preferably, the chemically inert, water-soluble salt does not undergo any chemical reaction with the other components present in the etching solution. In the context of the chemically inert, water-soluble salt, neither the dissociation of the salt upon dissolving in the etching solution nor a simple proton/ion exchange with the water or other components present in the etching solution are considered chemical reactions. As utilized herein, the term "water-soluble" refers to a salt having a solubility in water at typical etching temperatures (e.g., about 20-30° C.) that is sufficient to appreciably increase the ionic strength of the etching solution (e.g., a solubility in water at 25° C. of about 100 mg/L or more, about 1 g/L or more, about 10 g/L or more, or about 100 g/L or more). Preferably, the chemically inert, water-soluble salt comprises a conjugate base of an acid (e.g., a conjugate base of an inorganic acid). The chemically inert, water-soluble salt can comprise any suitable conjugate base of an acid including, but not limited to, sulfate ions ($SO_4^{2-}$), bisulfate ions ($HSO_4^{1-}$), chloride ions, phosphate ions ($PO_4^{3-}$), hydrogen phosphate ions ($HPO_4^{2-}$), dihydrogen phosphate ions ($H_2PO_4^{1-}$), nitrate ions ($NO_3^{1-}$), and mixtures thereof. When the chemically inert, water-soluble salt comprises a conjugate base of an acid, the chemically inert, water-soluble salt can comprise any suitable counterion including, but not limited to, aluminum ions, ammonium ions, copper ions, iron ions, lithium ions, magnesium ions, nickel ions, potassium ions, sodium ions, and mixtures thereof. Preferably, the chemically inert, water-soluble salt, when present, is a sulfate salt, and, more preferably, the sulfate salt is selected from the group consisting of aluminum sulfate, ammonium sulfate, copper sulfate (cupric sulfate), iron sulfate (ferrous sulfate), lithium sulfate, magnesium sulfate, nickel sulfate, potassium sulfate, sodium sulfate, and mixtures thereof. In another preferred embodiment, the chemically inert, water-soluble salt, when present, is selected from the group consisting of sodium chloride, sodium sulfate, sodium bisulfate, sodium phosphate, sodium hydrogen phosphate, sodium dihydrogen phosphate, sodium nitrate, potassium chloride, potassium sulfate, potassium bisulfate, potassium phosphate, potassium hydrogen phosphate, potassium dihydrogen phosphate, potassium nitrate, and mixtures thereof.

The chemically inert, water-soluble salt can be present in the etching solution in any suitable concentration. Typically, the concentration of the chemically inert, water-soluble salt in the etching solution is about 0.01 wt. % or more, preferably about 0.1 wt. % or more, more preferably about 0.2 wt. % or more, and most preferably about 0.5 wt. % or more. Furthermore, the concentration of the chemically inert, water-soluble salt in the etching solution can be as high as the solubility limit of the chemically inert, water-soluble salt in the etching solution, but typically is about 20 wt. % or less, preferably about 10 wt. % or less, more preferably about 6 wt. % or less, still more preferably about 5 wt. % or less, and most preferably about 3 wt. % or less.

The metallic orthopaedic implant is exposed to the etching solution for a time and under conditions sufficient to provide at least a portion of the metallic orthopaedic implant with a micron or nanometer-scale surface roughness. Typically, the implant is exposed to the etching solution for about 0.5 minute or more, preferably about 1 minute or more, and more preferably about 2 minutes or more (e.g., about 3 minutes or more). Furthermore, the implant typically is exposed to the etching solution for about 60 minutes or less, preferably about 30 minutes or less, and more preferably about 10 minutes or less (e.g., about 7 minutes or less, about 6 minutes or less, about 5 minutes or less, about 4 minutes or less, or about 3 minutes or less). The etching solution can be maintained at any suitable temperature. The temperature of the etching solution typically is about 20° C. or more, more preferably about 22° C. or more, and the temperature also typically is about 100° C. or less, more preferably about 30° C. or less.

Those of ordinary skill in the art will readily appreciate that the conditions and time required to impart the desired surface roughness to the metallic implant will depend upon several factors. For instance, the necessary amount of time will decrease as the concentration of the acid and fluoride salts present in the etching solution increases. Furthermore, the necessary amount of time will decrease as the temperature of the etching solution increases. Also, the amount of time necessary to impart the desired surface roughness to the metallic implant will depend on the particular metal(s) comprising the metallic body of the implant and the metallic elements adhered to the surface thereof. It has also been found that individually varying the concentration of any one of the acid, the fluoride salt, or the sulfate salt will impact the scale of the surface roughness produced on the surface of the metallic orthopaedic implant.

Preferably, the etching solution is agitated for at least a portion of the time during which the metallic orthopaedic implant is exposed to the etching solution. The etching solution can be agitated using any suitable means. For example, the etching solution can be agitated using a simple mechanical stirrer, such as a magnetic stirrer. Alternatively, the metallic orthopaedic implant can be moved within the etching solution to agitate the etching solution. Preferably, the etching solution is agitated by bubbling a gas through at least a portion of the etching solution. Any suitable gas can be bubbled through the etching solution including, but not limited to, air, argon, helium, nitrogen, oxygen, and mixtures thereof. Preferably, the gas bubbled through the etching solution comprises, consists essentially of, or consists of nitrogen. In addition to bubbling the gas through at least a portion of the etching solution, the headspace above the etching solution can be purged with the gas.

Any suitable apparatus or sparger can be used to bubble the gas through the etching solution. For example, the sparger can comprise a plurality of substantially parallel pipes disposed within the container holding the etching solution and positioned so that they are substantially or completely submerged in the etching solution while the metallic implant is exposed to the etching solution. In such an arrangement, each of the parallel pipes typically is connected to a gas supply, such as a manifold, and desirably comprises a plurality of perforations such that a pressurized gas contained within the internal volume defined by the interior surface of the pipe can pass through the perforations and into the environment surrounding the outer surface of the pipe. As noted above, the sparger can be positioned within the container holding the etching solution in any suitable position, provided that at least a portion of the sparger is submerged in the etching solution while the metallic implant is exposed to the etching solution. Preferably, the sparger is positioned within the container so that the pressurized gas in the sparger emerges from the perforations at a point in the container that is even with or lower than the level at which the metallic implant is positioned within the container while it is exposed to the etching solution.

The etching solution can be agitated for any suitable amount of time. In order to homogenize the etching solution before the metallic orthopaedic implant is exposed to the etching solution, the etching solution can be agitated for any suitable period of time (e.g., about 1 minute or more, about 5 minutes or more, or about 10 minutes or more) before the metallic orthopaedic implant is exposed to the etching solution. Once the metallic orthopaedic implant is exposed to the etching solution, the etching solution can be agitated for any suitable amount of time. For example, the etching solution can be agitated for the entire time during which the metallic orthopaedic implant is exposed to the etching solution. Preferably, the etching solution is agitated for only a portion of the time during which the metallic orthopaedic implant is exposed to the etching solution. In a preferred embodiment, the etching solution is agitated for about 5 minutes or less, more preferably about 3 minutes or less, and most preferably about 2 minutes or less (e.g., about 1 to about 2 minutes, or about 1 minute or less) from the moment the metallic orthopaedic implant is exposed to the etching solution.

The position of the metallic orthopaedic implant within the etching solution can affect the characteristics of the implant surface produced by the inventive method. For example, positioning the metallic orthopaedic implant close to the interface between the etching solution and the headspace above the etching solution (i.e., at the top of the container holding the etching solution) can produce a surface having a micron or nanometer-scale surface roughness better suited to facilitating the acceptance of tissue and bone growth after implantation than a metallic orthopaedic implant positioned toward the middle or bottom of the container holding the etching solution.

Furthermore, varying the surface area of the etching solution exposed to the headspace above the etching solution can affect the characteristics of the implant surface produced by the inventive method. For example, it has been found that, using the same composition and volume of etching solution, increasing the total volume of the container holding the etching solution can produce a metallic orthopaedic implant having a micron or nanometer-scale surface roughness better suited to facilitating the acceptance of tissue and bone growth after implantation than a metallic orthopaedic implant etched in a container having a smaller total volume.

The altered surface of the metallic implant, or the portion of the surface of the metallic body and metallic elements exposed to the etching solution, can be cleaned by any suitable method. Typically, the altered or exposed surface is thoroughly rinsed with water or a commercially available detergent, such as Alconox® (manufactured by Alconox, Inc.). If desired, any residual acid remaining on the altered or exposed surface of the implant can be neutralized by exposing the implant to a basic solution, such as a solution of sodium bicarbonate, or a solution containing a commercially available alkaline detergent, such as Alconox®, and then thoroughly rinsing the altered or exposed surface with water.

The resulting chemically-etched metallic orthopaedic implant can be dried by any suitable method. Typically, the implant is exposed to an environment that is maintained between approximately 22° C. and approximately 100° C. for about 30 minutes to about 24 hours.

As noted above, the method of the invention provides a metallic orthopaedic implant with a micron or nanometer-scale surface roughness while maintaining the structural integrity of, or without structural impairment to, the metallic orthopaedic implant. As utilized herein, the terms "maintaining the structural integrity" and "without structural impairment" are used to indicate that the inventive method does not etch significant amounts of the metal(s) comprising the metallic body of the implant or the metallic elements adhered to the surface thereof. In particular, the inventive method can be used to provide a metallic orthopaedic implant having a plurality of metallic elements adhered thereto with a micron or nanometer-scale surface roughness without etching a significant amount of the metal comprising the individual metallic elements and without compromising a significant portion of the "links" between the individual metallic elements or the "links" between the metallic elements and the surface of the implant. More particularly, and as, for example, when the metallic elements comprise spherical beads, attachment from sintering or other bonding between adjacent beads (as well as with the metallic body of the implant) involves only a minor part of the surface area of the attached elements. It thus becomes important to insure that these minor areas of attachment are not eliminated or reduced in the etching process so as to impair the structural integrity to an undesired level. Visually, the retention of structural integrity and/or lack of structural impairment can be seen by a comparison, before and after etching, using scanning electron microscopy in a straightforward manner.

As can be seen from the FIGURES and from the following Examples, use of the method of the invention provides a suitably roughened surface while maintaining the structural integrity of the implant. Generally, the structural integrity of the metallic implant (i.e., the structural integrity of the three-dimensional porous surface defined by the metallic body of the implant and the metallic elements adhered thereto) can be measured by determining the implants ability to withstand a shear force applied to the surface thereof. For example, the structural integrity of the metallic implant can be measured using any of the techniques for testing metallic coatings set forth in ASTM F1044-99 entitled, "Standard Test Method for Shear Testing of Calcium Phosphate Coatings and Metallic Coatings." Preferably, the structural integrity of the metallic orthopaedic implant is measured by embedding a portion of the metallic implant (i.e., a portion of the three-dimensional porous surface) in a curable material (e.g., acrylic resin), and then applying a load to the implant in a direction intended to pull the implant from the body of the curable material. The shear strength is considered to be within the ranges set forth herein when determined by any of the aforementioned techniques. Typically, a metallic orthopaedic implant which has been subjected to the chemical etching method of the invention can withstand a shear force of about 13,000 kPa (about 2,000 psi) or more, preferably about 20,000 kPa (about 3,000 psi) or more, and most preferably about 27,000 kPa (about 4,000 psi) or more.

In addition to providing a metallic orthopaedic implant with a micron or nanometer-scale surface roughness, the method of the invention can also provide the metallic orthopaedic implant with a surface comprising, consisting essentially of, or consisting of micron-scale surface texture, nanometer-scale surface texture, or a combination thereof. As utilized herein, the term "micron-scale surface texture" is used to describe a surface texture comprising, consisting essentially of, or consisting of surface features between about 100 nm and about 10 μm in size (e.g., surface features having an adjacent valley to adjacent peak height of about 100 nm to about 10 μm). The term "nanometer-scale surface texture" is used to describe a surface texture comprising, consisting essentially of, or consisting of surface features about 100 nm or less in size (e.g., surface features having a valley to peak height of about 100 nm or less). Preferably, about 50% or more (e.g., about 60% or more, about 70% or more, about 80% or more, about 90% or more, about 95% or more, about 98% or more, about 99% or more, about 99.5% or more, or about 100%) of the surface (e.g., as measured by the surface area) of the metallic orthopaedic implant of the invention comprises micron-scale surface texture, nanometer-scale surface texture, or a combination thereof.

The method of the invention also can improve the wettability of the surface of the metallic orthopaedic implant relative to the surface of a similar metallic orthopaedic implant that has not been subjected to the method of the invention and/or relative to the surface of a similar metallic orthopaedic implant that does not have a micron or nanometer-scale surface roughness. The relative wettability of the surface of a metallic orthopaedic implant can be determined using any suitable technique, such as measuring the angle of contact between the surface of the metallic orthopaedic implant and the surface of a water droplet placed on the metallic orthopaedic implant (i.e., the water contact angle). Preferably, the method of the invention lowers the water contact angle of the surface of the metallic orthopaedic implant relative to the surface of a similar metallic orthopaedic implant that has not been subjected to the method of the invention. The surface of the metallic orthopaedic implant of the invention preferably exhibits a lower water contact angle relative to the surface of a similar metallic orthopaedic implant that does not have a micron or nanometer-scale surface roughness.

It has been found that the etching required to provide the desired surface roughness can be carried out without the need to first remove any oxide surface layer that may be present as was considered essential in some prior techniques. More specifically, metals such as titanium will readily build up an oxide surface layer upon exposure to air. Yet, contrary to prior techniques that first required removal of this oxide layer, the use of the invention is transparent with respect to the presence of an oxide layer. In other words, the desired surface roughening is achieved whether the metallic body of the implant being treated has an oxide surface layer or not.

Further, one prior technique, rather than removing the oxide layer, utilizes treatment conditions to alter the crystalline phase of the titanium oxide layer from the native oxide layer (i.e., the oxide which occurs naturally upon exposure to the atmosphere) to an oxide having what is considered to be a more desirable crystalline phase or other characteristics. No such alteration is required with the invention. The chemical etching is simply carried out under conditions sufficient to achieve the desired roughness.

The invention thus provides a metallic orthopaedic implant, which can be prepared by the present method. The inventive orthopaedic implant comprises (i) a metallic body having a surface and (ii) metallic elements adhered to a portion of the surface of the metallic body to define a three-dimensional porous surface geometry, wherein at least some of the metallic elements are interconnected to provide pores between adjacent metallic elements, the pores being 10 microns or greater in size, and wherein at least some of the metallic elements have a micron or nanometer-scale surface roughness. Inasmuch as the surface roughness desirably is achieved utilizing chemical etching in accordance with the method of the invention, the implant is "free of particles," i.e., the resulting implant does not contain any residual particles as would be present when the surface roughening was achieved by blasting with an erosive blasting media, such as metal oxide particles.

The metallic orthopaedic implant described herein can further comprise at least one bioactive coating on the surface thereof. More specifically, a bioactive coating can be applied to the surface of the metallic orthopaedic implant described herein after the surface of the implant has been altered to provide a micron or nanometer-scale surface roughness. The implant of the invention exhibits improved adhesion of bioactive coatings as compared to implants having surface roughness values ($R_a$) of greater than 10 μm. While not wishing to be bound to any particular theory, it is believed that the scale of the surface roughness ($R_a \leq 10$ μm) provides a surface to which the bioactive coating can anchor itself, providing for increased strength and adhesion.

As utilized herein, the term "bioactive coating" is used to refer to any biocompatible coating which can be applied to the surface of an orthopaedic implant and promotes the attachment of soft tissue, the growth of bone, and/or the apposition of bone at the surface of the implant after implantation. Suitable bioactive coatings include, but are not limited to, calcium phosphate materials (e.g., hydroxyapatite), bioactive glasses, glass ceramics, biopolymers, extracted proteins, recombinant proteins, peptides, growth factors, an oxide layer on the surface of the metallic orthopaedic implant, and mixtures thereof. The bioactive coating(s) can be applied by any suitable method. Such methods include, but are not limited to, plasma spraying, dipping and sintering, hot isostatic pressing, physical vapor deposition, sol-gel, electrophoretic deposition, electrochemical deposition, electrocodeposition, anodization and hydrothermal precipitation, blast coating, pulsed laser deposition, biomimetic deposition, and combinations thereof. When the bioactive coating comprises an oxide layer on the surface of the metallic orthopaedic implant, the oxide layer can have any suitable thickness. Preferably, the thickness of the oxide layer on the surface of the metallic orthopaedic implant is about 5 nm to about 5 μm (e.g., about 5 nm to about 4 μm, or about 10 nm to about 3 μm). The oxide layer can be applied to the surface of the metallic orthopaedic implant using any suitable method. Suitable methods include, but are not limited to, exposing the surface of the metallic orthopaedic implant to an alkaline solution for a time sufficient to produce an oxide layer having the desired thickness, heating the metallic orthopaedic implant in an oxygen-containing atmosphere (e.g., air, pure oxygen, etc.) for a time and under conditions sufficient to produce an oxide layer having the desired thickness, or any suitable combination thereof.

The inventive method can also be used to provide a micron or nanometer-scale surface roughness to metallic orthopaedic implants having a complex surface geometry. As utilized herein, the term "complex surface geometry" refers to the surface of a metallic orthopaedic implant incorporating structures and/or surface features that are sized or oriented in such a way that they cannot be effectively textured using any of the known mechanical or line-of-sight methods. The method of the invention is especially well suited to etching such implants because the relatively mild chemical action of the etching solution does not significantly etch the metal comprising the structures and/or surface features. Accordingly, the inventive method imparts a micron or nanometer-scale surface roughness without significantly compromising the structural integrity of the metallic orthopaedic implant.

Even further, and while finding particular advantages when used with implants having either a three-dimensional porous or complex surface geometry, it has been found that the method of the invention can also be advantageously employed to process any type of metallic implant. No pretreatment is necessary to remove, or alter, any native oxide layer present.

In particular, the aforementioned etching solution can be used to provide a metallic orthopaedic implant having a native oxide surface layer with a micron or nanometer-scale surface roughness to facilitate acceptance of tissue and bone growth after implantation while maintaining the structural integrity of the implant. To that end, the invention provides a method comprising the steps of (a) providing a metallic implant having a native oxide surface layer a portion thereof to be altered to provide a micron or nanometer-scale surface roughness, (b) exposing the portion of the surface layer to an etching solution comprising (i) at least one fluoride salt, (ii) at least one acid, and (iii) water for a time and under conditions sufficient to provide the implant with the micron or nanometer-scale surface roughness while maintaining structural integrity of the orthopaedic implant, (c) cleaning at least the exposed surface, and (d) drying the thus-etched metallic implant.

The method of the invention provides a reliable, and easily controllable, process to accomplish the desired surface roughness. The process is readily amenable to commercial production, providing superior efficiency.

Additionally, the inventive method is especially well suited to providing a micron or nanometer-scale surface roughness to implants that have been roughened or textured by other techniques which produce surface roughness values ($R_a$) greater than 0.5 μm. For instance, the inventive method can be used to provide a micron or nanometer-scale surface roughness to the surface of a metallic implant which has previously been roughened by high-pressure blasting using an erosive blasting media, such as metal oxide particles. The inventive method can also be used to further etch the surface of implants that have previously been textured by machining, high-pressure liquid jets, or any other suitable technique. Furthermore, while not wishing to be bound to a particular theory, it is believed that the chemical action of the inventive method, when used to further etch the surface of an implant that has previously been textured, removes a significant portion of the contaminants or residue that can become embedded in the surface features created by the initial texturing process, thereby providing an improved surface for the acceptance of bone and tissue growth after implantation.

The following examples further illustrate the invention but, of course, should not be construed as in any way limiting its scope.

EXAMPLE 1

This example demonstrates the chemical etching process of the invention. A polished Ti6A14V coupon was exposed to an etching solution containing 1 wt. % NaF and 0.25 N HCl for approximately five minutes at 25° C. After etching, the coupon was removed from the etching solution, thoroughly rinsed with water, and dried. The resulting coupon had a micron-scale surface roughness having a surface roughness value ($R_a$) of approximately 180 nm. SEM micrographs of the surface of the chemically etched coupon are provided in FIGS. 1A (2000× magnification) and 1B (5000× magnification).

EXAMPLE 2

Figure 2:
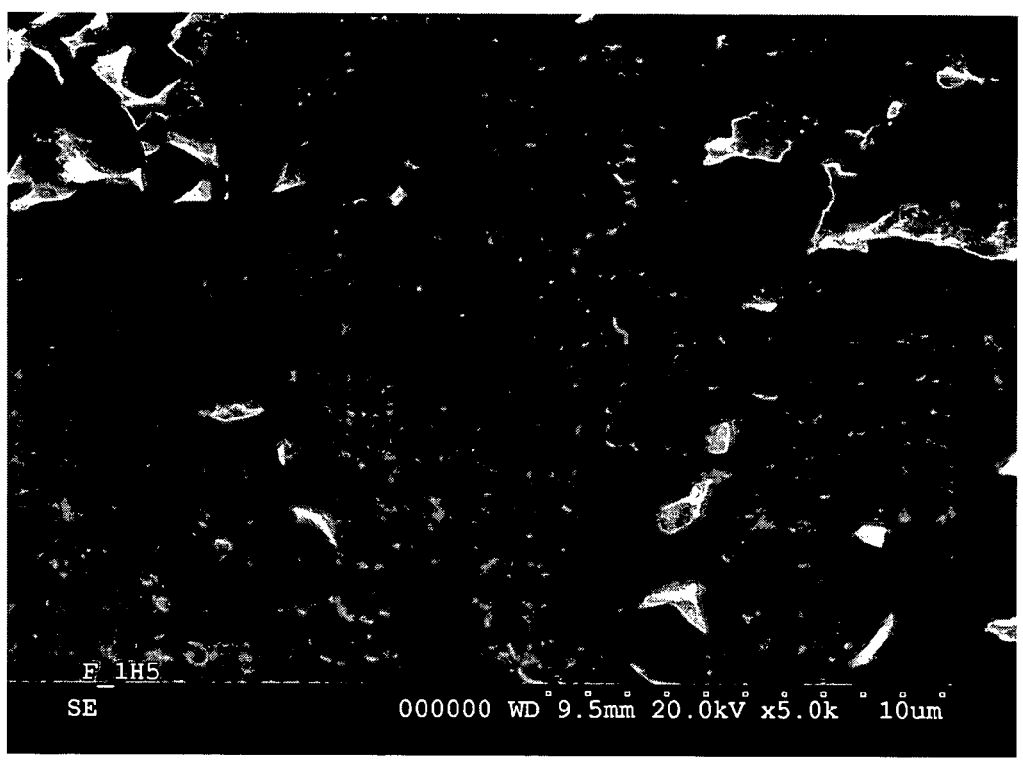
FIG. 2 is an SEM micrograph (5,000 times magnification) of the surface of a polished Ti6A14V coupon which has been chemically etched using the method of the invention.

This example demonstrates the chemical-etching process of the invention. A polished Ti6A14V coupon was exposed to an etching solution containing 0.1 wt. % NaF and 0.25 N HCl for approximately five minutes at 25° C. After etching, the coupon was removed from the etching solution, thoroughly rinsed with water, and dried. The resulting coupon had a nanometer-scale surface roughness having a surface roughness value ($R_a$) of approximately 60 nm. An SEM micrograph of the surface of the chemically etched coupon is provided in FIG. 2.

EXAMPLE 3

Figure 3A:
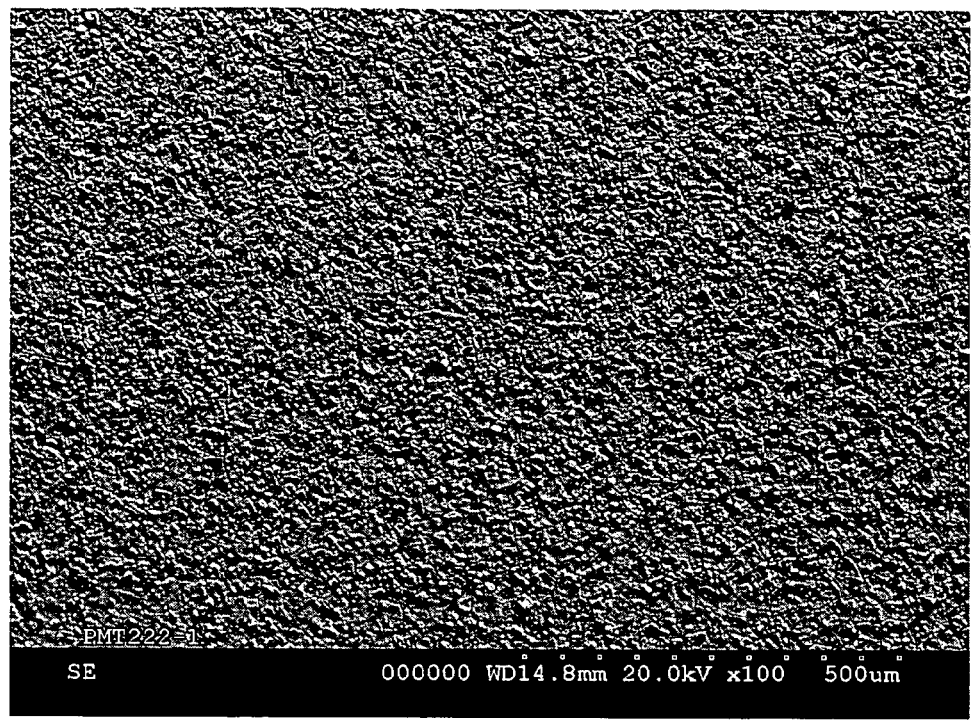
FIG. 3A is an SEM micrograph (100 times magnification) of the surface of a polished Ti6A14V coupon which has been coated with a biomimetic apatite (approximately 8 μm in thickness) using a solution that mimics the conditions in the human body.

This example demonstrates the improved adhesion exhibited by bioactive coatings applied to the orthopaedic implant of the invention. An approximately 8 μm thick biomimetic apatite coating was applied to a polished Ti6A14V coupon and the chemically etched coupon of Example 1 using a solution that mimics the conditions in the human body. The surfaces of the coupons were then analyzed using scanning electron micrography (SEM) and Energy Dispersive Spectroscopy (EDS) to determine the presence of the elements comprising an apatite coating. The SEM micrographs and EDS spectrum for the polished coupon are provided in FIGS. 3A and 3B, respectively, and the SEM micrographs and EDS spectrum for the chemically etched coupon are provided in FIGS. 4A and 4B, respectively. As can be seen from FIGS. 3B and 4B, each of the coated coupons exhibited strong peaks corresponding to calcium and phosphorous, which indicated the presence of a significant apatite coating on the surface of each coupon. Each of the coated coupons was then covered with a piece of cellulose adhesive tape, and the tape was then peeled from the surface of the coated coupons. The surface of each coupon was then analyzed using SEM and EDS, and the results were compared to the measurements obtained before application and peeling of the cellulose adhesive tape to determine the effects on the apatite coating. The SEM micrographs and EDS spectrum for the polished coupon are provided in FIGS. 5A and 5B, respectively, and the SEM micrographs and EDS spectrum for the chemically etched coupon are provided in FIGS. 6A and 6B, respectively.

Figure 3B:
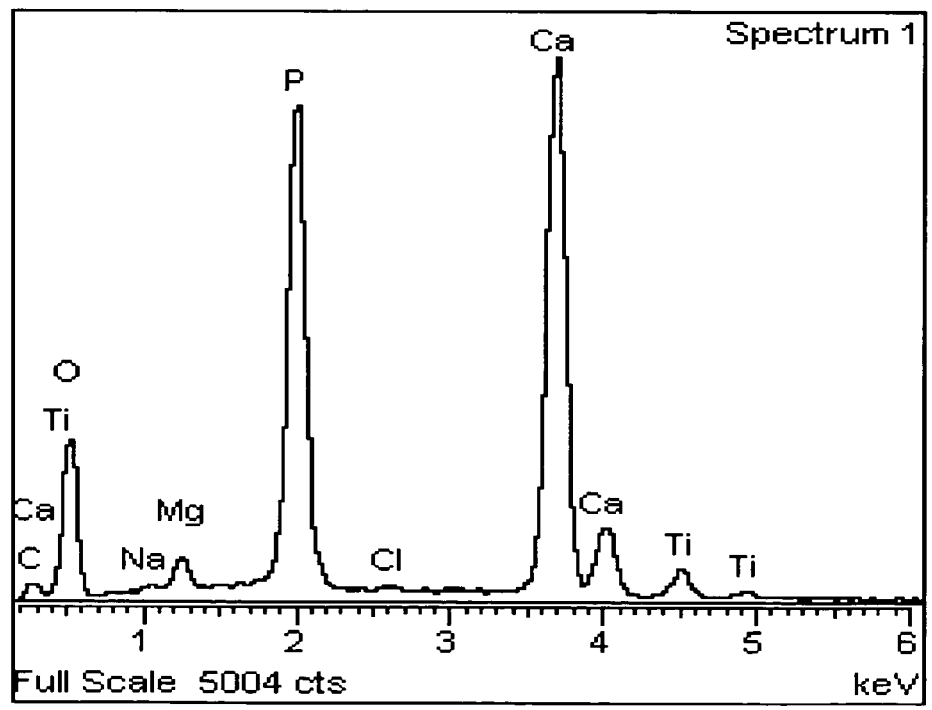
FIG. 3B is an Electron Dispersive Spectroscopy (EDS) spectrum of the surface of the polished Ti6A14V coupon shown in FIG. 3A.
Figure 4A:
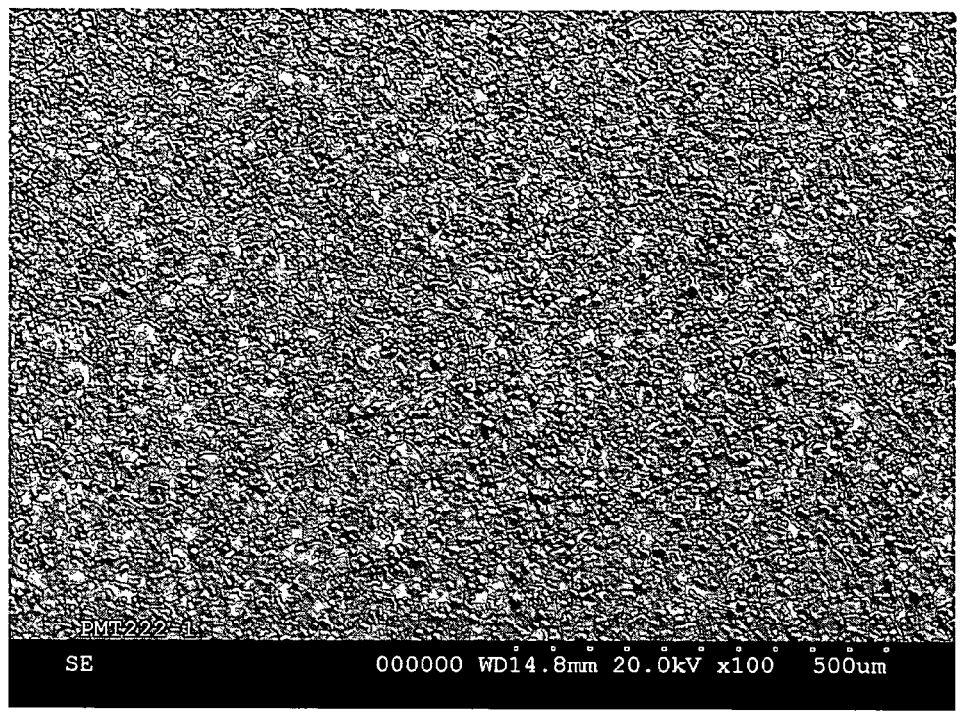
FIG. 4A is an SEM micrograph (100 times magnification) of the surface of a Ti6A14V coupon which has been coated with a biomimetic apatite (approximately 8 μm in thickness) using a solution that mimics the conditions in the human body. Before application of the hydroxyapatite coating, the Ti6A14V coupon was chemically etched using the method of the invention to provide a micron-scale surface roughness having a surface roughness value ($R_a$) of approximately 180 nm.
Figure 4B:
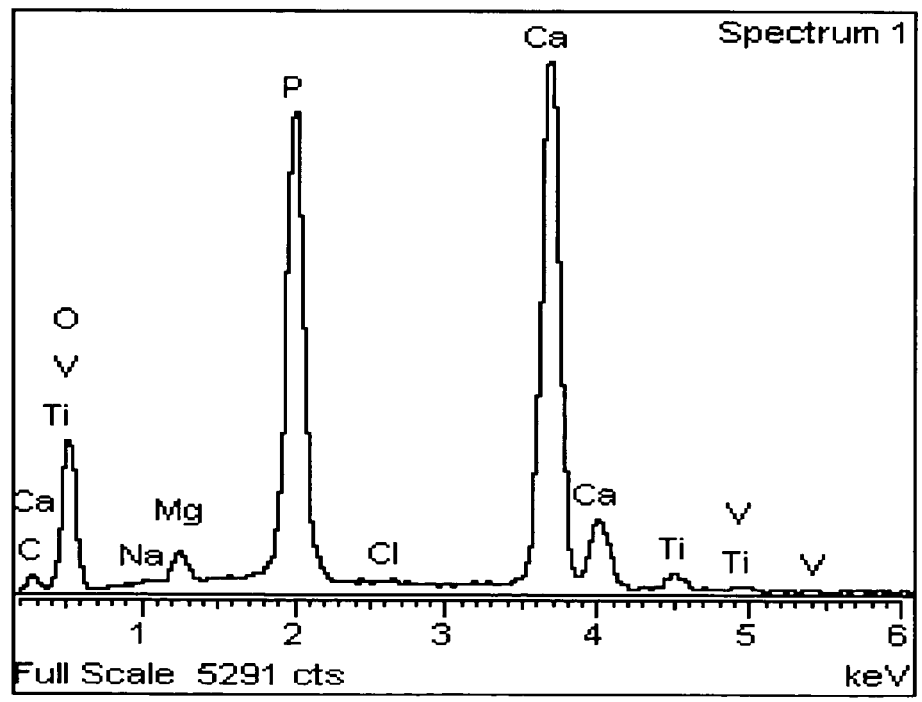
FIG. 4B is an EDS spectrum of the surface of the Ti6A14V coupon shown in FIG. 4A.
Figure 5A:
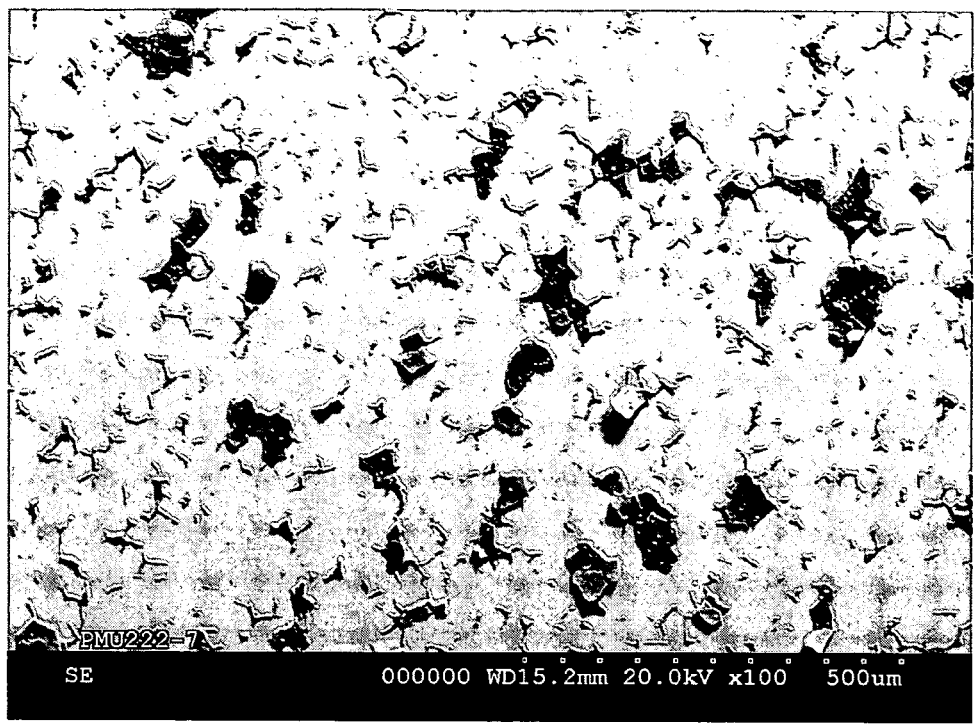
FIG. 5A is an SEM micrograph (100 times magnification) of the surface of the polished Ti6A14V coupon shown in FIG. 3A after the application and removal of a piece of cellulose adhesive tape to the surface thereof.
Figure 5B:
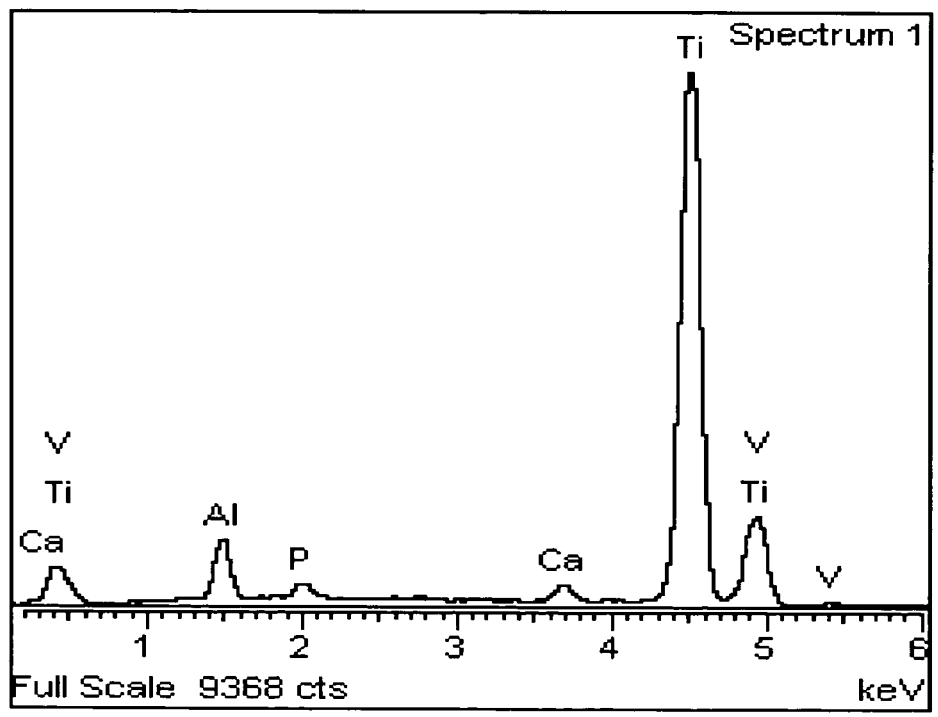
FIG. 5B is an EDS spectrum of the surface of the Ti6A14V coupon shown in FIG. 5A.
Figure 6A:
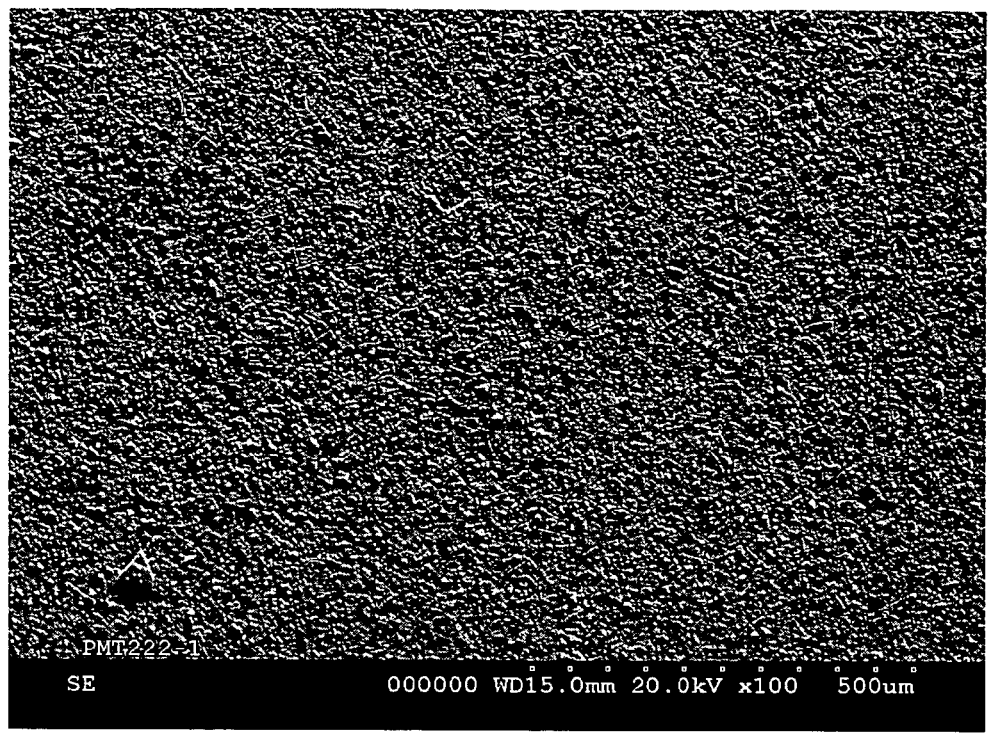
FIG. 6A is an SEM micrograph (100 times magnification) of the surface of the Ti6A14V coupon shown in FIG. 4A after the application and removal of a piece of cellulose adhesive tape to the surface thereof.
Figure 6B:
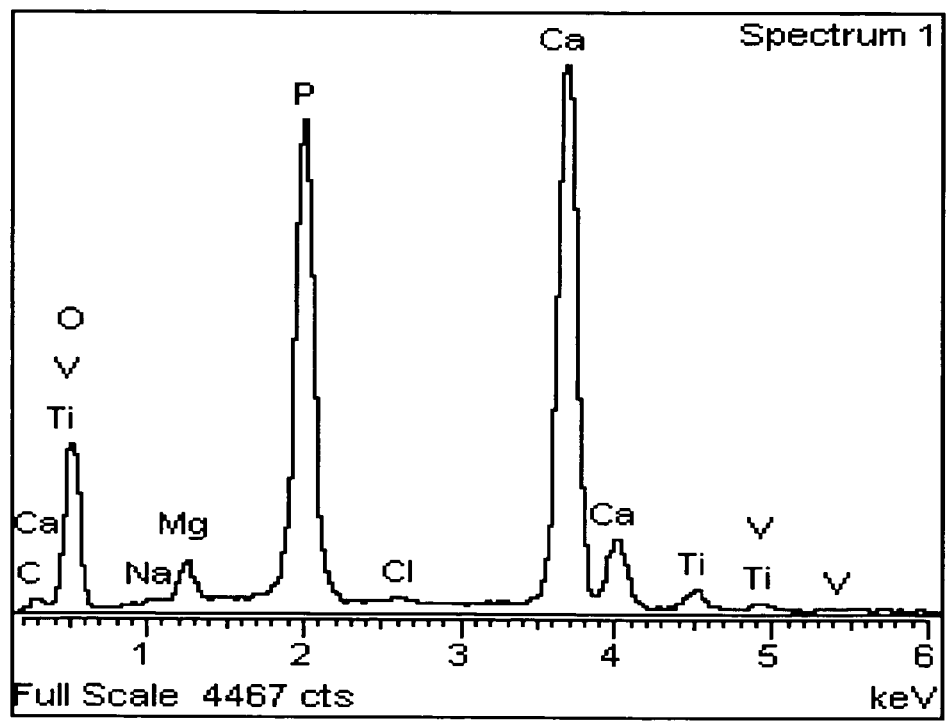
FIG. 6B is an EDS spectrum of the surface of the Ti6A14V coupon shown in FIG. 6A.

As evidenced by a comparison of FIGS. 3B and 5B, the polished coupon exhibited sharp decreases in the peaks for calcium and phosphorous following application and removal of the cellulose adhesive tape, indicating that a significant portion of the apatite coating had been removed. Furthermore, FIGS. 3A and 5A reveal that a significant portion of the apatite coating was removed by the application and removal of the cellulose adhesive tape. However, as can be seen from FIGS. 4B and 6B, the chemically etched coupon exhibited only minor decreases in the peaks for calcium and phosphorous following application and removal of the cellulose adhesive tape, indicating that a substantial portion of the apatite coating remained adhered to the chemically etched coupon. FIGS. 4A and 6A also reveal that the apatite coating was not significantly affected by the application and removal of the cellulose adhesive tape. These results indicate that the metallic orthopaedic implants of the invention provide for better adhesion of bioactive coatings.

EXAMPLE 4

This example demonstrates a method of chemically etching the surface of a metallic orthopaedic implant according to the invention. A commercially available porous coated proximal sleeve (S-ROM®, DePuy Orthopaedics, Inc.), which comprises a metallic body having a plurality of metallic beads adhered to the surface thereof, was analyzed using SEM to determine surface morphology. As can be seen from FIG. 7A, the surface of the proximal sleeve comprises a plurality of metallic beads having a diameter of approximately 100-300 μm, which are adhered to the surface of the metallic body. Furthermore, FIG. 7B shows that the surface of the proximal sleeve has no observable surface roughness.

The proximal sleeve was then exposed to an etching solution containing 1 wt. % NaF and 0.25 N HCl for approximately five minutes at 25° C. After etching, the sleeve was removed from the etching solution, thoroughly rinsed with water, and dried. SEM micrographs of the chemically etched sleeve were then obtained to determine the surface morphology of the sleeve after the etching treatment. These SEM micrographs are provided in FIGS. 8A and 8B.

Figure 7A:
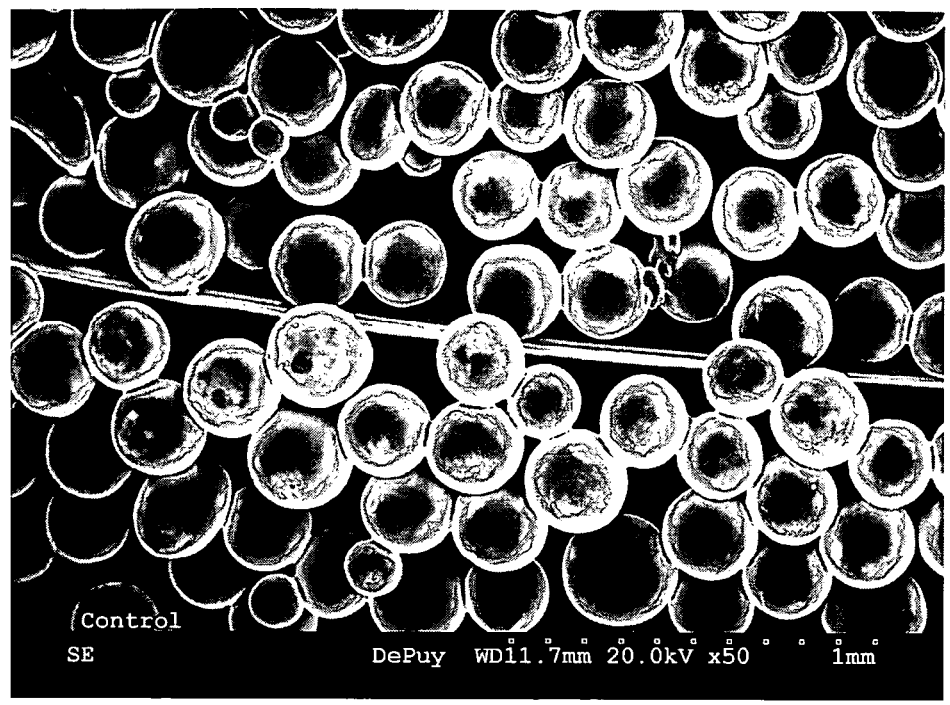
FIG. 7A is an SEM micrograph (50 times magnification) of the surface of a commercially available porous coated proximal sleeve (S-ROM®, DePuy Orthopaedics, Inc.), which comprises a metallic body having a plurality of metallic beads adhered to the surface thereof.
Figure 7B:
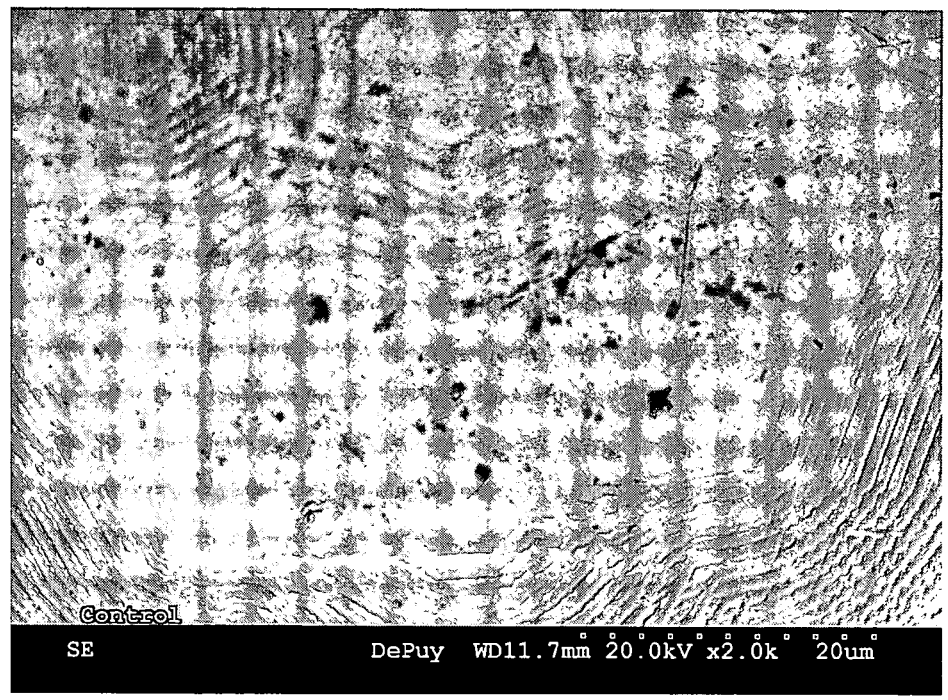
FIG. 7B is an SEM micrograph (2,000 times magnification) of the surface of the proximal sleeve shown in FIG. 7A.
Figure 8A:
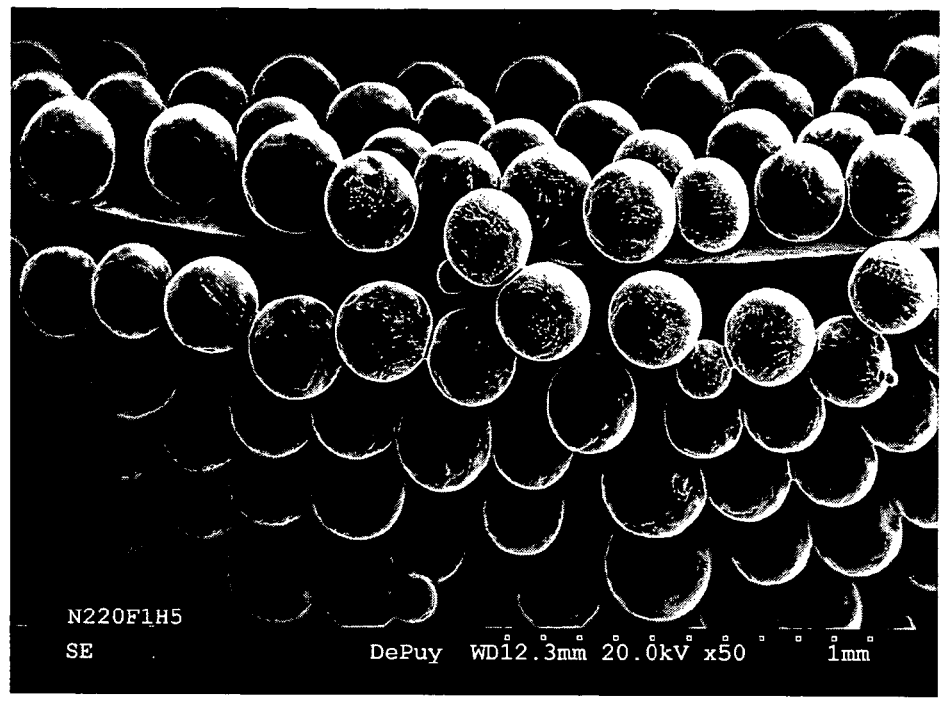
FIG. 8A is an SEM micrograph (50 times magnification) of the surface of the proximal sleeve shown in FIG. 7A after the proximal sleeve has been chemically-etched using the method of the invention to provide a micron or nanometer-scale surface roughness.
Figure 8B:
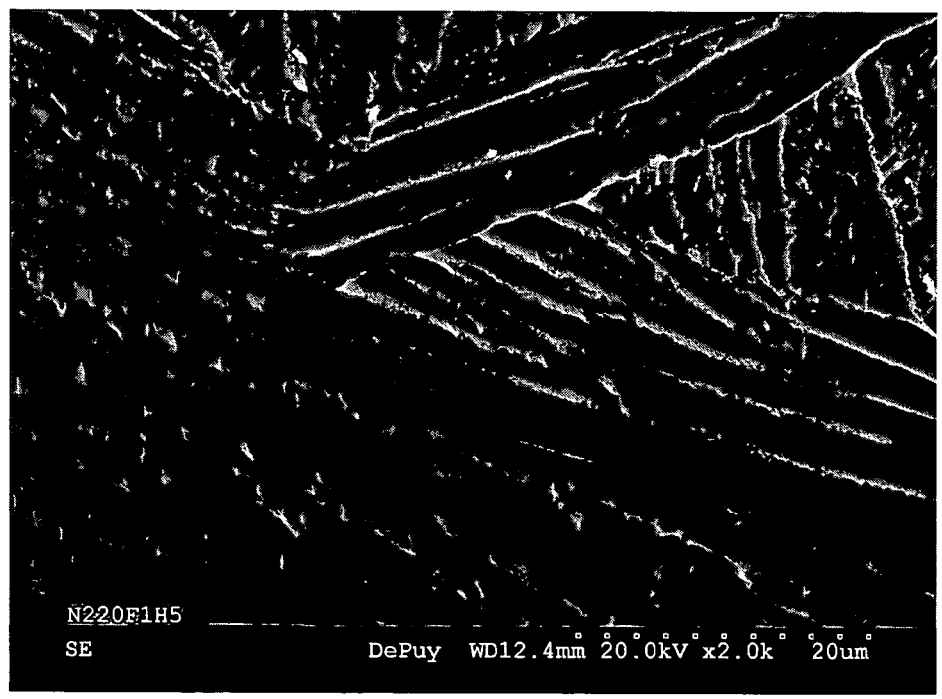
FIG. 8B is an SEM micrograph (2,000 times magnification) of the surface of the proximal sleeve shown in FIG. 8A.

Upon comparison, FIGS. 7A and 8A indicate that the porous structure of the sleeve (i.e., the metallic beads adhered to the surface of the implant) was not adversely affected by the chemical etching treatment. Furthermore, a comparison of FIGS. 7B and 8B reveals that the surface of the individual beads had been etched to provide a micron or nanometer-scale surface roughness. These results indicate that the method of the invention can be used to provide a metallic orthopaedic implant with a micron or nanometer-scale surface roughness while maintaining the structural integrity of the orthopaedic implant.

EXAMPLE 5

This example demonstrates that the method of the invention does not significantly affect the structural integrity of the surface of a metallic orthopaedic implant comprising a metallic body and a plurality of metallic elements adhered thereto. A porous, titanium bead coating was applied to one end of twelve Ti6A14V test pins (approximately 100 mm long and 6 mm in diameter) by applying and sintering a plurality of titanium beads to the surface of the individual test pins. The resulting surface geometry of each test pin was similar to the surface geometry of the proximal sleeve described in Example 4.

The coated portions of six of the Ti6A14V test pins were then subjected to light grit blasting to further texture the porous coated surface. Next, each of the coated test pins was chemically etched in a solution containing 0.5 wt. % NaF, 1 N HCl, and 2 wt. % $Na_2SO_4$. The test pins were exposed to the etching solution for approximately 5 minutes at a temperature of about 25° C.

The coated portion of each test pin was then placed in a separate vessel containing a freshly mixed self-curing acrylic resin (KoldMount™, Vernon-Benshoff Company, Albany, N.Y.). The resin was allowed to cure for 24 hours at 25° C., and then each of the test pins was removed from its respective vessel. The test pins were then subjected to a shear force of approximately 27,000 kPa (about 4,000 psi) under a load of approximately 44 kN (about 10,000 lbs.) using an MTS Sintech 10 electromechanical UTS (MTS Systems Corporation, Eden Prairie, Minn.).

Each of the twelve test pins was able to withstand the shear force applied thereto. More specifically, none of the test pins exhibited discernible signs of failure in the chemically etched portion of the three-dimensional porous surface geometry defined by the metallic body of the implant and the metallic elements (i.e., titanium beads) adhered to the surface thereof. These results indicate that the method of the invention can be used to provide a metallic orthopaedic implant with a micron or nanometer-scale surface roughness while maintaining the structural integrity of the orthopaedic implant.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of providing a metallic orthopaedic implant with a micron or nanometer-scale surface roughness to facilitate acceptance of tissue and bone growth or apposition after implantation, which method comprises the steps of:
   (a) providing a metallic orthopaedic implant comprising a metallic body having a surface and metallic elements adhered to at least a portion of the surface of the metallic body to define a three-dimensional porous surface geometry and
   (b) exposing at least a portion of the surface and metallic elements to an etching solution comprising (i) at least one fluoride salt, (ii) at least one acid selected from the group consisting of hydrochloric acid, sulfuric acid, and nitric acid and mixtures thereof, (iii) a sulfate salt, and (iv) water for a time and under conditions sufficient to etch the surface and provide the implant with micron or nanometer-scale surface roughness, wherein the acid is present in the etching solution at a concentration of 0.1 N or more.

2. The method of claim 1, wherein the concentration of the fluoride salt is about 0.1 to about 3 wt. % of the etching solution, and the concentration of the acid in the etching solution is 0.1 to about 2 N.

3. The method of claim 1, wherein the concentration of the fluoride salt is about 0.1 to about 3 wt. % of the etching solution, the concentration of the sulfate salt is about 0.5 to about 5 wt. % of the etching solution, and the concentration of the acid in the etching solution is 0.1 to about 2 N.

4. The method of claim 1, wherein the metallic body comprises a metal selected from the group consisting of titanium, titanium alloys, tantalum, tantalum alloys, stainless steel, and cobalt-chromium alloys.

5. The method of claim 1, wherein the fluoride salt is selected from the group consisting of ammonium fluoride, copper fluoride, potassium fluoride, sodium fluoride, zinc fluoride, and mixtures thereof.

6. The method of claim 1, wherein the sulfate salt is selected from the group consisting of aluminum sulfate, ammonium sulfate, copper sulfate, iron sulfate, lithium sulfate, magnesium sulfate, nickel sulfate, potassium sulfate, sodium sulfate, and mixtures thereof.

7. The method of claim 1, wherein the metallic elements comprise metallic particles.

8. The method of claim 7, wherein the metallic particles comprise metallic beads.

9. The method of claim 1, wherein the etching solution further comprises a chemically inert, water-soluble salt.

10. The method of claim 9, wherein the chemically inert, water-soluble salt is selected from the group consisting of sodium chloride, sodium sulfate, sodium nitrate, potassium chloride, potassium sulfate, potassium nitrate, and mixtures thereof.

11. The method of claim 9, wherein the concentration of the chemically insert, water-soluble salt is about 0.5 to about 6 wt. % of the etching solution.

12. The method of claim 1, wherein the etching solution is agitated while the metallic orthopaedic implant is exposed to the etching solution in step (b).

13. The method of claim 12, wherein the etching solution is agitated by bubbling an inert gas through the etching solution.

14. The method of claim 1, further including (c) cleaning at least the portion of the surface and metallic elements exposed to the etching solution.

15. The method of claim 14, further including (d) drying the metallic orthopaedic implant.

16. A method of providing a metallic orthopaedic implant having a native oxide surface layer with a micron or nanometer-scale surface roughness to facilitate acceptance of tissue and bone growth or apposition after implantation, which method comprises the steps of:
   (a) providing a metallic implant having a native oxide surface layer and at least a portion thereof to be altered to provide a micron or nanometer-scale surface roughness,
   (b) exposing the portion of the surface layer to an etching solution comprising (i) at least one fluoride salt, (ii) at least one acid selected from the group consisting of hydrochloric acid, sulfuric acid, and nitric acid and mixtures thereof, (iii) a sulfate salt, and (iv) water for a time and under conditions sufficient to etch at least a portion of the native oxide surface layer and provide the implant with the micron or nanometer-scale surface roughness, wherein the acid is present in the etching solution at a concentration of 0.1 N or more.

17. The method of claim 16, wherein the concentration of the fluoride salt is about 0.1 to about 3 wt. % of the etching solution, and the concentration of the acid in the etching solution is 0.1 to about 2 N.

18. The method of claim 16, wherein the concentration of the fluoride salt is about 0.1 to about 3 wt. % of the etching solution, the concentration of the sulfate salt is about 0.5 to about 5 wt. % of the etching solution, and the concentration of the acid in the etching solution is 0.1 to about 2 N.

19. The method of claim 16, wherein the metallic implant comprises a metal selected from the group consisting of titanium, titanium alloys, tantalum, tantalum alloys, stainless steel, and cobalt-chromium alloys.

20. The method of claim 16, wherein the fluoride salt is selected from the group consisting of ammonium fluoride, copper fluoride, potassium fluoride, sodium fluoride, zinc fluoride, and mixtures thereof.

21. The method of claim 16, wherein the sulfate salt is selected from the group consisting of aluminum sulfate, ammonium sulfate, copper sulfate, iron sulfate, lithium sulfate, magnesium sulfate, nickel sulfate, potassium sulfate, sodium sulfate, and mixtures thereof.

22. The method of claim 16, wherein the etching solution further comprises a chemically inert, water-soluble salt.

23. The method of claim 22, wherein the chemically inert, water-soluble salt is selected from the group consisting of sodium chloride, sodium sulfate, sodium nitrate, potassium chloride, potassium sulfate, potassium bisulfate, potassium nitrate, and mixtures thereof.

24. The method of claim 22, wherein the concentration of the chemically insert, water-soluble salt is about 0.5 to about 6 wt. % of the etching solution.

25. The method of claim 16, wherein the etching solution is agitated while the metallic orthopaedic implant is exposed to the etching solution in step (b).

26. The method of claim 25, wherein the etching solution is agitated by bubbling an inert gas through the etching solution.

27. The method of claim 16, further including (c) cleaning at least the portion of the surface and metallic elements exposed to the etching solution.

28. The method of claim 27, further including (d) drying the metallic orthopaedic implant.

29. A method of providing a metallic orthopaedic implant with a micron or nanometer-scale surface roughness to facilitate acceptance of tissue and bone growth or apposition after implantation, which method comprises the steps of:
(a) providing a metallic orthopaedic implant comprising a metallic body having a surface and metallic elements adhered to at least a portion of the surface of the metallic body to define a three-dimensional porous surface geometry and
(b) exposing at least a portion of the surface and metallic elements to an etching solution comprising (i) at least one fluoride salt, (ii) at least one acid, (iii) a sulfate salt, and (iv) water for a time and under conditions sufficient to etch the surface and provide the implant with micron or nanometer-scale surface roughness, wherein the acid is present in the etching solution at a concentration of 0.1 N or more.

30. A method of providing a metallic orthopaedic implant having a native oxide surface layer with a micron or nanometer-scale surface roughness to facilitate acceptance of tissue and bone growth or apposition after implantation, which method comprises the steps of:
(a) providing a metallic implant having a native oxide surface layer and at least a portion thereof to be altered to provide a micron or nanometer-scale surface roughness and
(b) exposing the portion of the surface layer to an etching solution comprising (i) at least one fluoride salt, (ii) at least one acid, (iii) a sulfate salt, and (iv) water for a time and under conditions sufficient to etch at least a portion of the native oxide surface layer and provide the implant with the micron or nanometer-scale surface roughness, wherein the acid is present in the etching solution at a concentration of 0.1N or more.

* * * * *